United States Patent [19]

Pasternack et al.

[11] Patent Number: 5,017,489
[45] Date of Patent: May 21, 1991

[54] CYTOTOXIC T LYMPHOCTE SERINE ESTERASE AND METHOD FOR STIMULATION AND INHIBITION

[75] Inventors: Mark S. Pasternack, Brookline; Herman S. Eisen, Waban, both of Mass.

[73] Assignee: Massachusetts Institute of Technology, Cambridge, Mass.

[21] Appl. No.: 234,906

[22] Filed: Aug. 22, 1988

[51] Int. Cl.$^5$ .................. C12N 9/16; C12N 9/48; A61K 39/395; A61K 39/44
[52] U.S. Cl. ................. 435/196; 435/212; 435/213; 435/226; 424/85.8; 424/85.91; 530/387; 530/388
[58] Field of Search ............ 435/196, 212, 213, 226; 424/85.8, 85.91; 530/387, 388

[56] References Cited

U.S. PATENT DOCUMENTS 4,515,893 5/1985 Kung et al.
4,550,086 10/1985 Reinherz et al.

OTHER PUBLICATIONS

Redelman, D. et al., (1980) J. Immunol 124, 870–878.
Wofsy, D. et al. (1987) J. Immunol, 138, 3247–3253.
Grau, G. E. et al., (1986) J. Immunol. 137, 2348–2354.
Buchmeier, N. A. et al., (1985) Proc. Nat. Acad. Sci., U.S.A. 82, 7404–7408.
Shiohara, T. et al., (1988) J. Immunol. 141, 2261–2267.
Wofsy, D. et al., (1985) J. Exper. Med. 161, 378–391.
Cosimi, A. B. et al., (1981) N. Engl. J. Med. 305(6), 308–314.

*Primary Examiner*—Elizabeth C. Weimar
*Assistant Examiner*—Charles L. Patterson
*Attorney, Agent, or Firm*—Kilpatrick & Cody

[57] ABSTRACT

Antibodies, nucleic acid sequences, and methods for inhibition of lysis for a novel serine esterase produced by both murine and human cytotoxic T lymphocytes. The serine esterase has an apparent molecular weight of approximately 28,000–31,000, as determined by SDS gel electrophoresis under reducing conditions, and trypsin-like activity. Inhibition of the esterase correlates with inhibition of the cells' cytolytic activity. Specific inhibition of the serine esterase is useful as a method for immunosuppression as well as for the inhibition of cytolytic activity of T lymphocytes, both in vivo and in vitro. The genes encoding the murine and human serine esterase are homologous.

12 Claims, 2 Drawing Sheets

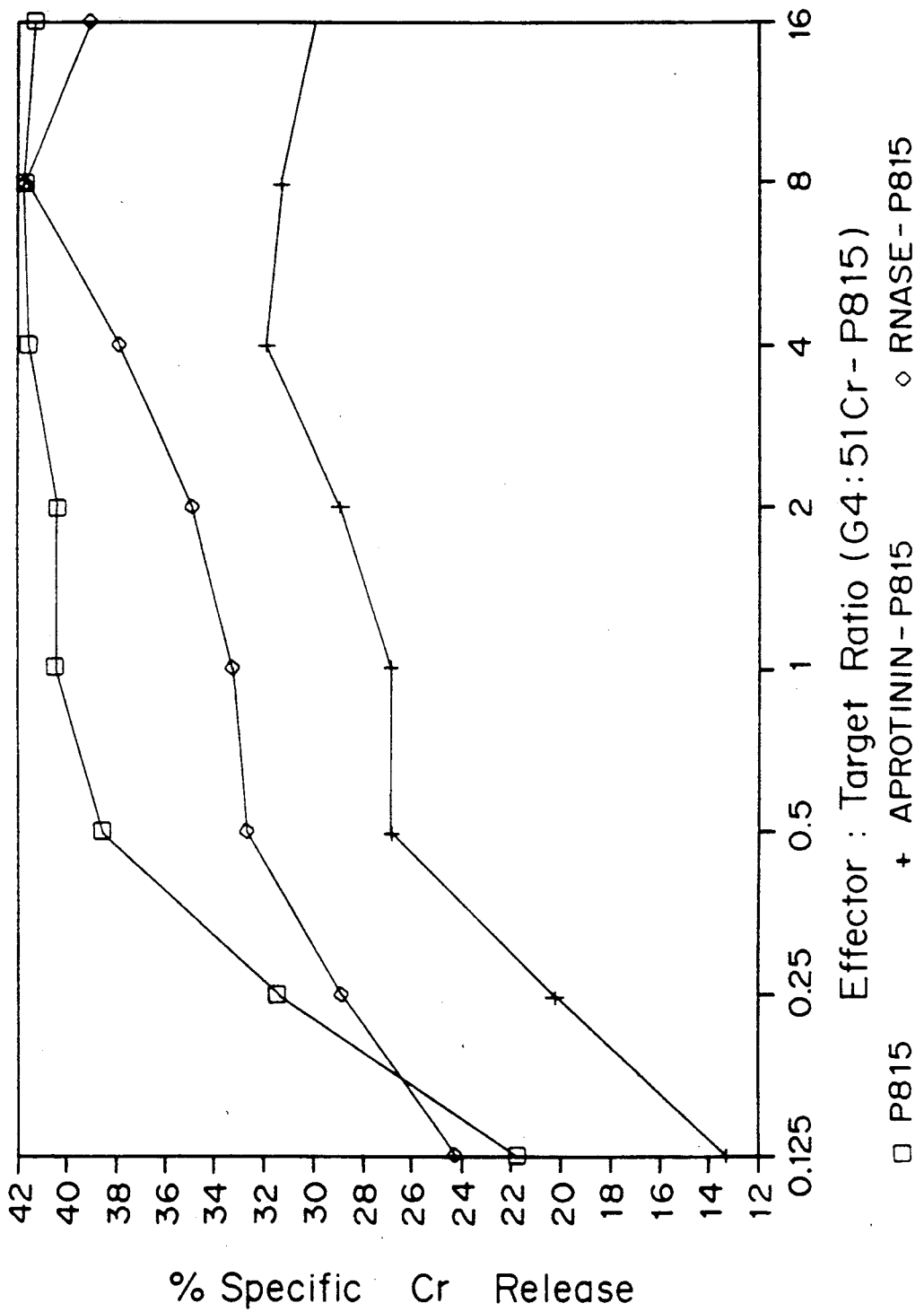

CYTOTOXIC T LYMPHOCTE SERINE ESTERASE AND METHOD FOR STIMULATION AND INHIBITION

The U.S. Government has rights in this invention by virtue of National Cancer Institute Grant No. CA-15472; CA-28900; and CA-14051.

This invention relates generally to the field of purified proteins and in particular to a purified serine esterase of cytotoxic T lymphocyte origin.

BACKGROUND OF THE INVENTION

This application is a continuation-in-part divisional of U.S. Ser. No. 750,323 filed June 28, 1985 by Mark S. Pasternack and Herman N. Eisen entitled "Cytotoxic T Lymphocyte Serine Esterase and Method for Stimulation and Inhibition", now U.S. Pat. No. 4,783,410 issued Nov. 8, 1988.

The vertebrate immune system is characterized by its ability to respond to an enormously diverse set of antigenic determinants. This capability is due to the synthesis by the body of a set of glycoproteins whose specificity for a single antigen is determined by a variable sequence of amino acids which binds to the antigen. The antigen-recognizing glycoproteins produced by B cells are called immunoglobulins. T cells or thymus derived lymphocytes are also capable of recognizing a wide range of different antigens. As in B cells, the ability to recognize a given antigen is also fixed in any particular clonal line. T cells, however, characteristically recognize only antigens located on the surfaces of cells in the specific molecular context of self major histocompatibility complex (MHC) gene products, not as freely circulating antigens. These cells provide a number of different mechanisms for defending the host against invasion by foreign substances and aid in limiting the frequency of tumors (neoplasms).

Unfortunately, these defense mechanisms can create problems, both when they are directed against their own host and when it becomes desirable to maintain foreign cells within the host, as in organ transplantation. Present immunosuppressive therapy following organ transplantation is based on corticosteroids and cyclosporine. In addition to their numerous non-immunologic side effects, these agents produce nonselective immunosuppression. As a result, life threatening infections, often due to pathogens of ordinarily low virulence ("opportunistic infections"), are a major problem in the management of allograft recipients. These problems are discussed by R.H. Rubin in "Infection in the renal transplant patient", *Approach to Infection in the Compromised Host*, R. H. Rubin and L. S. Young, eds., pp. 553–605 (New York, Plenum Medical Book Company, 1981). For example, cyclosporin has been associated with direct nephrotoxicity and an increased rate of lymphoid neoplasms.

When thymus-derived cells are stimulated by various agents, they differentiate into helper, suppressor, or cytotoxic T lymphocytes. Cytotoxic T lymphocytes (CTL) recognize and lyse target cells and are also thought to serve as an important source of defense against viral infections and possibly against neoplasms. A. E. Lukacher, V. L. Braciale, and T. J. Braciale in *J. Exp. Med.*, 160, 814–824 (1984) and H. D. Engers, A. L. Glasebrook, and G. D. Sorenson in *J. Exp. Med.*, 156, 1280–1285 (1982), review theories and supporting evidence.

The nature of the receptors responsible for antigen-recognition by these cells is rapidly becoming clarified, but the molecular mechanisms responsible for their cytolytic activity remain largely unknown. The possibility that proteases may be involved in this process has been suggested due to the effects of certain inhibitors. T-W Chang and H. N. Eisen, in *J. Immunol.*, 124, 1028–1033 (1980) and D. Redelman and D. Hudig in *J. Immunol.*, 124, 870–878(1980) demonstrated that the lytic activity of cytotoxic T lymphocytes (CTL) is reduced by exposure to certain protease inhibitors. Similar results have been shown for natural killer cells by D. Hudig, T. Haverty, C. Fulcher, D. Redelman, and J Mendelsohn, in *J. Imunol.*, 126, 1569–1574 (1981); P-C. Quan, T. Ishizaka, and B. R. Bloom in *J. Immunol.*, 128, 1786–1791 (1982); and D. Hudig, D. Redelman, and L. Minning in *J. Immunol.*, 133, 2647–2654 (1984).

In U.S. Ser. No. 750,323 filed June 28, 1985 by Mark S. Pasternack and Herman N. Eisen entitled "Cytotoxic T Lymphocyte Serine Esterase and Method for Stimulation and Inhibition", applicants described the isolation and characterization of a serine esterase having trypsin-like activity which is produced predominantly by cytotoxic T lymphocytes.

It is an object of the present invention to produce antibodies or other inhibitors to the serine esterase produced by the cytotoxic T lymphocytes.

Another object of the present invention is to produce nucleotide sequences encoding the serine esterase produced by the cytotoxic T lymphocytes, or portions thereof.

A further object of the present invention is to provide a means for inhibition of the cytolytic activity of the cytotoxic T lymphocytes.

A still further object of the present invention is to provide a mechanism for preventing and monitoring allograft rejection.

SUMMARY OF THE INVENTION

The present invention are antibodies to, inhibitors of, and nucleotide sequences encoding a purified 28,000–31,000 dalton (apparent molecular weight) protein with serine esterase activity which is produced by lymphocytes, primarily cytotoxic T lymphocytes (CTL), and, in much smaller quantities, other lymphocytes, and methods for use thereof. The serine esterase has been variously referred to as Granzyme A, T cell specific protease-1 (TSP-1), and BLT-serine esterase (referring to its ability to cleave N-α-benzyloxycarbonyl-L-lysine thiobenzyl ester).

The 28,000–31,000 dalton apparent molecular weight serine esterase, originally isolated from clones of murine CTL, possesses considerable trypsin-like esterase activity. This activity is blocked completely by two serine esterase inhibitors, diisopropylfluorophosphoridate (DFP) and phenylmethylsulfonyl fluoride (PMSF), but not by N-α-tosyl lysyl chloromethyl ketone (TLCK).

Cloned human T cell lines contain a homologue of the murine T cell-specific serine esterase. The human and murine enzymes are similar in several respects: (a) both are expressed in T cells but not in B cells; (b) they have similar patterns of inhibition by small organic molecules (i.e., they are inhibited by PMSF and DFP, but not by TLCK or TPCK); (c) both enzymes can be affinity labeled with [$^3$H]DFP; (d) SDS-PAGE analysis under reducing conditions reveal the labeled proteins to have similar apparent molecular weights ($M_r$ approximately 30,000 for the human enzyme and $M_r$ approximately 30–34,000 for the murine enzyme); (e) a cDNA clone from a library prepared from a human cloned T cell line (HE 14) hybridizes with two synthetic oligonucleotide probes that correspond to nucleotide sequences surrounding the active site serine and histidine of the HF gene, which encodes the principal murine T cell-specific BLT-serine esterase; and (f) just as the BLT-serine esterase activity in murine thymocytes increases markedly after stimulation with Con A, the activity in human peripheral blood lymphocytes also increases after allogeneic stimulation.

The serine esterase is present in a variety of T lymphocyte populations.

Conventional polyclonal and monoclonal antibodies are produced against the CTL serine esterase using standard immunization techniques. Nucleotide sequences encoding the esterase and polypeptide components of the esterase, and probes, are also produced using standard techniques.

In vivo and in vitro immunosuppression is achieved by selective inhibition of the CTL serine esterase. Two types of serine esterase inhibitors can be used in vivo: small molecular weight molecules that can diffuse into the cells and larger molecules which are bound to the surface of either the target cell or the CTL. With respect to the latter, monoclonal antibodies or agents such as aprotinin, which inhibit the protein at the active site, can be used to decrease or completely stop lytic activity. The antibodies against the protein are also useful in diagnosis and monitoring, especially of graft rejection.

BRIEF DESCRIPTION OF THE DRAWING

FIG. 2 is a graph comparing inhibition of lysis of modified P815 target cells by CTL clone G4, as a function of effector cell:target cell (G4:$^{51}$Cr-P815):

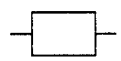

Figure 1:
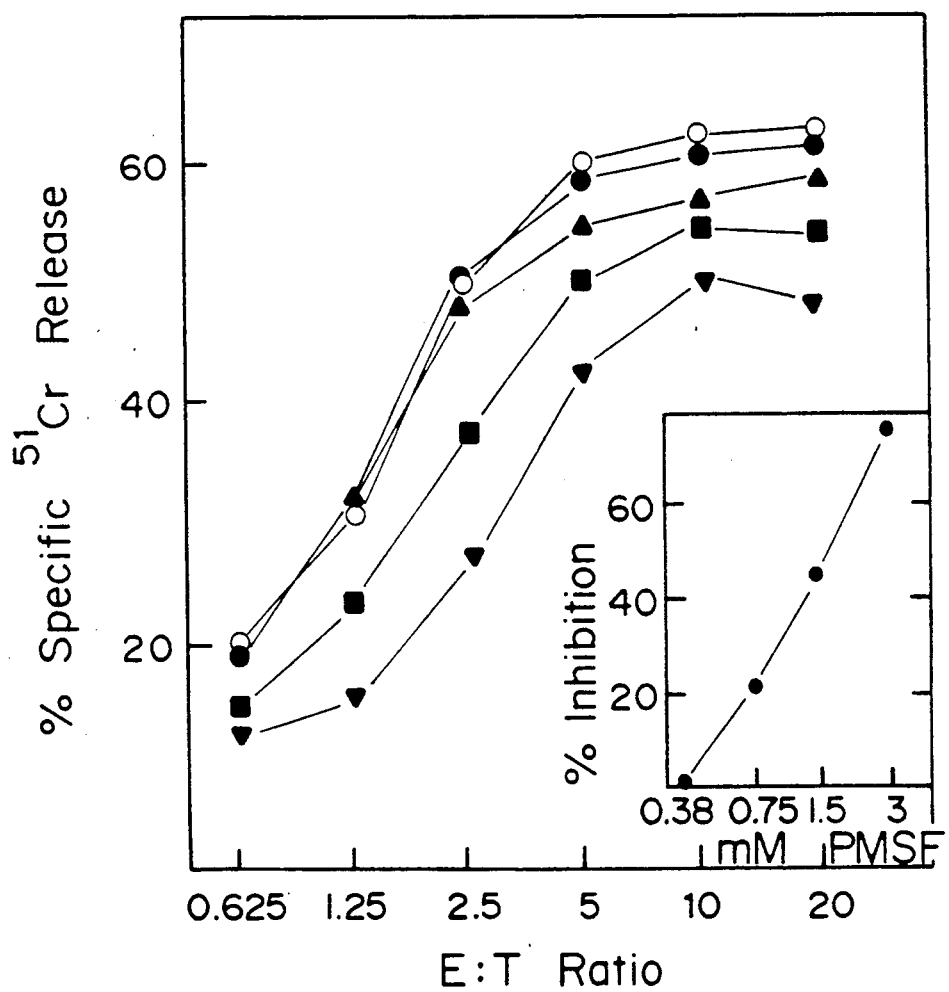
FIG. 1 is a graph of inhibition by PMSF of specific target cell lysis by CTL clone G4, as a function of PMSF concentration.

P815 control;

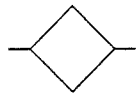

RNAse treated P815; -+- effector cell:aprotinin bound target cell.

DETAILED DESCRIPTION OF THE INVENTION

The present invention is a purified 28,000–31,000 dalton molecular weight protein with serine esterase activity which is produced by T lymphocytes, primarily cytotoxic T lymphocytes (CTL) and, in much smaller quantities, other lymphocytes.

Cytotoxic T lymphocytes (CTLs) are prominent components of immune defenses against virus infections because of their ability to destroy virus-infected cells. Extensive studies indicate that when the cells of cloned murine CTL cell lines tightly adhere to and recognize epitopes on another cell (a target cell), dense cytoplasmic granules within the CTL migrate towards and discharge their contents at the CTL-target cell junction. One component of the granules is a complement (C9)-like hemolytic protein (termed perforin or cytolysin) that can form nonspecific ion channels in cell membranes contributing to target cell death.

The granules also contain large amounts of a neutral serine esterase that cleaves the synthetic lysine derivative benzyloxycarbonyl-L-lysine-thiobenzyl ester (BLT). The enzyme, referred to here as BLT-serine esterase, is one of the most abundant proteins (approximately 1%) in murine CTL cell lines and appears to be involved in target cell destruction.

Isolation and Characterization of Murine Serine Esterase

Extracts of G4 cells, a clone of BALB.B anti H-2D$^d$ CTL described by M. S. Pasternack, M. V. Sitkovsky, and H. N. Eisen in *J. Immunol.*, 131, 2477–2483 (1983), were prepared in phosphate-buffered saline (PBS) containing 0.5% Nonidet-P40 (NP-40). The technique used is as follows.

G4 cells, which are adherent, are harvested by brief exposure to EDTA (5 mM in PBS) after decanting stimulator cell debris. Cells are washed twice in fresh medium, twice in PBS or in RPMI 1640 containing 100 μg/ml bovine serum albumin (5x recrystallized, Boehringer-Mannheim, Indianapolis, IN), counted, washed a third time in PBS, and then lysed by incubation of 1–2×10$^7$ cells/ml in PBS containing 0.5% NP-40 (Particle Data Laboratories, Elmhurst, IL) for 20–30 minutes on ice with frequent vortexing.

Trypsin-like esterase activity in the lysate is assayed spectrophotometrically by means of a sensitive coupled reaction involving N-α-benzyloxycarbonyl-L-lysine thiobenzyl ester (BLT), as described by Green and Shaw in *Anal. Biochem.*, 93, 223–226 (1975). Hydrolysis of BLT yields benzyl mercaptan, which reacts with Ellman's reagent to produce the thiophenoxide chromophore.

Specifically, esterase activity is measured by adding 900 μl of a reaction mixture consisting of 0.2 M Tris HCl, pH 8.1; 2×10$^{-4}$ M BLT [Calbiochem-Behring, San Diego, CA] and 2.2×10$^{-4}$ M dithiobis [nitrobenzoic acid] [Sigma Chemical Co., St. Louis, MO], to 100 μl of appropriate dilutions of cell extracts in NP-40/PBS. After 30 minutes at room temperature, the absorbance at 412 nm is measured in a Gilford spectrophotometer using 100 μl 0.5% NP-40 in PBS plus 900 μl of the reaction mixture as a blank. One unit of esterase activity is defined as an absorbance of 1.0.

The assay results for the following cell extracts or cell extracts plus inhibitors are listed in Table 1. The cell extracts were prepared from (1) G4, a BALB.B anti H-2D$^d$ CTL clone, described by Pasternack et al. in *J. Immunol.*, 131, 2477–2483 (1983); (2) G4 grown in recombinant human IL-2; (3) B10, a BALB.B anti H-2L$^d$ CTL clone, also described by Pasternack et al. in *J. Immunol.*, 131, 2477–2483 (1983); (4) 1.5.2, a BALB.B anti H2L$^d$ CTL clone; (5) cr 15, a (B10.BRxB10.D2)F$_1$ anti-BALB minor CTL clone described by Hunig and Bevan, in *J. Exp. Med.*, 155, 111–125 (1982); (6) O$_5$, a Balb/c T$_h$ clone specific for ovalbumin plus Ia$^d$ described by C. Clayberger et al. in *J. Immunol.*, 133 1174–1178 (1984); (7) D$_5$, a (Balb/cxA/J)F$_1$ T$_h$ clone specific for arsanilated protein plus Ia$^d$ described by Rao et al. in *J. Exp. Med.*, 159, 479–494 (1984); (8) A$_6$A$_2$, a T$_h$ hybridoma of B10.A origin fused with BW5147, specific for hen egg lysozyme, provided by Dr. L. Glimcher; (9) EL-4, a T cell leukemia of C57 BL/6 origin; (10) EL-4 maintained in 10% RCASUP; (11) BW5147, T cell lymphoma of AKR origin; (12) BW5147 maintained in 10% RCASUP; (13) BW5147 maintained in 10% RCASUP and 10 μg/ml Con A; (14) P815, mastocytoma of DBA/2 origin; (15) thymocytes harvested from 3-week old BALB/c females; (16) thymocytes cultured for 4 days with 10% RCASUP and 10 μg/ml Con A, described by Irle et al. in *J. Exp. Med.*, 148, 32–45 (1978); (17) BALB/c spleen cells following lysis of erythrocytes with $NH_4Cl$; (18) BALB/c spleen cells depleted of T cells by treatment with two anti-Thy 1 monoclonal antibodies and rabbit complement; (19) BALB/c spleen cells cultured for 4 days with *S. Typhosa* lipopolysaccharide (Difco Laboratories, Detroit, MI), 10 μg/ml, then depleted of T cells with anti-Thy 1 and complement before assay; (20-22) B cell clones of CBA/N mice described by J. Braun in *J. Immunol.*, 130, 2113-2116 (1983).

For the inhibition studies, an aliquot of G4 extract is incubated for 30 minutes at 37° with DMSO or DMSO containing serine esterase inhibitors. Percent inhibition is calculated as (1-[absorbance of treated samples/absorbance of control sample]) ×100: (23) G4 extract pretreated with 2 mM DFP; (24) G4 extract pretreated with 2mM PMSF; and (25) G4 extract pretreated with $5\times10^{-4}$ M TLCK.

TABLE 1

Esterase activity in extracts of cytotoxic T lymphocytes and other cells

| Cells | Units/$10^6$ Cell Equivalents |
|---|---|
| Cytotoxic T Lymphocyte Clones: | |
| 1. G4 | 172–311 |
| 2. G4 (IL-2) | 203.4 |
| 3. B10 | 67.4 |
| 4. 1.5.2 | 84.3 |
| 5. Cr-15 | 77.6 |
| Noncytotoxic T Lymphocytes: | |
| 6. O3 | 0.520 |
| 7. D5 | 0.431 |
| 8. $A_6A_2$ | 0.202 |
| 9. EL-4 | 0.572 |
| 10. EL-4 (RCASUP) | 0.800 |
| 11. BW5147 | 0.258 |
| 12. BW5147 (RCASUP) | 0.268 |
| 13. BW5147 (RCASUP + Con A) | 0.365 |
| Other: | |
| 14. P815 | 0.518 |
| 15. Thymocytes | 0.040 |
| 16. Con A-activated thymocytes | 3.47 |
| 17. Resting spleen cells | 0.557 |
| 18. Splenic B cells | 0.323 |
| 19. Splenic LPS blasts | 0.136 |
| 20. B cell clone 670.6 | 0.259 |
| 21. B cell clone 670.11 | 0.251 |
| 22. B cell clone 750.17 | 0.227 |
| Inhibition Studies | Percent Inhibition |
| 23. G4 (DFP-treated) | 98.7 |
| 24. G4 (PMSF-treated) | 97.2 |
| 25. G4 (TLCK-treated) | 4.6 |

As shown in Table 1, the esterase activity, equivalent to approximately 1 μg of trypsin/$10^6$ cells, was not restricted to G4, since three other CTL clones, B10, 1.5.2, and cr 15, of two different specificities, had roughly comparable activity.

Since all of the CTL clones had been maintained in long-term culture in medium containing 10% rat spleen cell Concanavalin A (Con A) supernatant (RCASUp) and stimulator cells, the stimulator cells and a variety of other cell lines were assayed for esterase activity. The BTL-esterase activities in NP-40 extracts of several different non-cytotoxic cell lines are also summarized in Table 1. The cells used as stimulators to maintain the cultured CTL clones, BALB/c spleen cells and in vitro passaged P815, possess little activity. Two T cell tumor lines, EL-4 and BW5147, also have minimal activity. Furthermore, when these T cell lines are maintained in medium containing 10% RCASUP, or when BW5147 is incubated with both 10% RCASUP and 10 μg/ml Con A, there is no significant increase in enzyme activity. These results establish that the presence of stimulator cells and conditioned medium are not sources of adsorbed esterase activity.

The endogenous character of the esterase activity in CTL is confirmed by two further observations. First, there is no difference between the esterase activity in G4 cells that have been serially cultured twice in recombinant human interleukin-2 (Biogen, Cambridge, MA) and in those that are cultured continuously in 10% RCASUP. Second, two T helper cell $T_h$ clones, 03 and D5, that have been maintained in long-term culture with 10% CASUP and intermittently stimulated with antigen-pulsed spleen cells, have negligible activity. A T helper cell hybridoma, $A_6A_2$, also has only traces of activity. Thus, among all B and T lymphocytes tested, a high level of esterase activity is expressed only in CTL.

The expression of esterase activity in CTL generated by short-term culture of precursor cells was also measured using the following method. Thymocytes were incubated in culture medium containing RCASUP and Con A, using the method of C. Irle, P-F. Piquet, and P. Vassalli in *J. Exp. Med.*, 148, 32–45 (1978). After four days, viable thymocytes were found to have a level of lectin-dependent cytotoxic activity of 1–4 lytic units ($[LU_{50}]/10^6$ cells measured by the method of J. C. Cerottini, and K. Brunner in *Adv. Immunol.*, 18, 67-132 (1974)). This is comparable to what is seen in conventional mixed lymphocyte cultures. Extracts of these thymocytes have an approximately 50-fold increase in BTL-esterase activity.

As shown in Table 1, the CTL esterase activity is completely inhibitable by the irreversible serine esterase inhibitors DFP and PMSF. It is not, however, inhibited by TLCK, a trypsin inhibitor known to block CTL cytotoxicity and to react with the surface glycoproteins T200 and LFA-1, described by T-W. Chang, and H. N. Eisen in *J. Immunol.*, 124, 1028-1033 (1980); D. Redelman and D. Hudig in *J. Immunol.*, 124, 870-878 (1980); and M. S. Pasternack, M. V. Sitkovsky, and H. N. Eisen in *J. Immunol.*, 131, 2477-2483 (1983).

Additional studies showed that the serine esterase was also not inhibited by 5 mM TLCK in DMSO nor by $a_2$ macroglobulin at 125 μg/ml. However, it was essentially totally inhibited by 234 Kallikrein units of Trasylol (aprotinin).

$^3$H-DFP was used as an affinity-labeling reagent according to the method of L. W. Heck, E. Remond-O'Donnell, and H. G. Remold in *Biochem. Biophys. Res. Comm.*, 83, 1576-1583 (1978) to further characterize the esterase. Although minor $^3$H-labeled components were identified at Mr=76,000 and 71,000, the prominent $^3$H-DFP-reactive component was observed at Mr=28,000. The higher molecular weight moieties were present at about the same low level in all lymphoid cells tested. However, the level of the 28,000 dalton component clearly varied with the level of the BLT-esterase activity: both were pronounced in extracts of CTL clones but present in only trace amounts in noncytotoxic cells, and both increased after CTL activity was induced in thymocytes by incubation with Con A.

Further evidence linking the serine esterase activity to the 28,000 dalton protein is provided by their copurification through an affinity chromatography column and an ion-exchange column using the following method.

Greater than $10^9$ adherent G4 cells are harvested by brief exposure to EDTA after decanting stimulator cell debris. The cells are washed twice by centrifugation in complete medium, once in Hanks' balanced salt solution containing 0.1 mg/ml bovine serum albumin, and finally resuspended in phosphate buffered saline (PBS) diluted with 1/10 volume 35 mM $MgCl_2$ and 100 mM HEPES pH 7.4 ("lysis buffer"). The cells are then disrupted at 4° C. with constant stirring by nitrogen cavitation at 300 lbs/in² for 15 minutes. The lysate is centrifuged at 2000 rpm for 7 minutes to yield a nuclear pellet and a post nuclear supernatant. The nuclear pellet is extracted twice with additional lysis buffer and the supernatants pooled with the post nuclear supernatant. The membrane fraction, which contains greater than 99% of the esterase activity, is sedimented at 100,000 g for 1 hour and resuspended in PBS containing 0.5% NP-40 and 0.02% sodium azide (PNA). The suspension is clarified by low speed centrifugation before chromatography.

The membrane fraction is slowly loaded onto a column of lentil lectin-sepharose (Pharmacia Fine Chemicals, Piscataway, NJ) containing approximately 10 ml of resin. The column is then washed extensively with PNA and esterase activity eluted by washing the column with PNA containing 0.5 M alpha methyl mannoside. The eluate fractions containing esterase activity are pooled and dialyzed against Tris HCl 15 mM pH 8.1 containing 0.02% sodium azide.

The dialyzed material is then loaded onto a column of lysine sepharose containing approximately 5 ml of resin. Following extensive washing with 15 mM Tris-HCl pH 8.1, 1% octyl glucoside, 0.02% sodium azide (TOA), esterase activity is eluted by a 60 ml 0-500 mM NaCl gradient in TOA. Esterase activity is monitored in the eluate and the peak fractions pooled. Analysis of the eluted material by SDS-polyacrylamide gel electrophoresis under reducing conditions reveals a protein at greater than 80% purity.

Complete purification is possible using preparative acrylamide gel electrophoresis under nonreducing conditions or gel filtration in the presence of octyl glucoside or by affinity chromatography using monoclonal anti-esterase antibodies coupled to sepharose as an immunosorbent.

Preparation of Antibodies to the Serine Esterase

Antibodies specific for CTL esterase can be prepared against the 80% or purer serine esterase. One method for making antibody is as follows: 100-200 μg of protein eluted from the lysine Sepharose column is concentrated by ultrafiltration, emulsified with complete Freund's adjuvant, and administered intradermally to each of two rabbits. The injections are repeated with the esterase in incomplete Freund's adjuvant at monthly intervals. Immune sera is collected one week after each injection and screened with an immunoprecipitation assay using G4 CTL extracts treated with $^3$H-DFP as a source of $^3$H esterase and with a solid phase radioimmunoassay using goat anti-rabbit antibodies as a capture antibody, followed by incubation with test sera and probing with $^{125}$I-labeled esterase.

Rabbit antibodies to the individual polypeptides can also be prepared. The polypeptides are separated using preparative SDS-polyacrylamide gel electrophoresis under reducing conditions. The gels are stained, the appropriate bands cut out, and the crushed acrylamide emulsified with adjuvant for immunization as described above. Immune serum is screened by solid phase radioimmunoassay using separate $^{125}$I-labeled polypeptides as probes.

A method for preparing anti-esterase monoclonal antibodies is as follows: rats are immunized subcutaneously with 50 μg of protein eluted from the lysine sepharose column emulsified with complete Freund's adjuvant. Immunization is repeated at 1 month intervals. After assays of test bleedings reveal evidence of antibodies to the esterase, the rats receive a final booster immunization. Four days later spleen and lymph nodes are removed. B cells recovered from these tissues are fused with a suitable myeloma partner, such as P3X63 Ag8-653, to produce hybridomas. Using standard procedures familiar to those skilled in the art, hybridomas secreting monoclonal antibodies to the esterase can be identified, cloned, expanded and used to produce large amounts of the antibody.

Antibodies have a number of uses in diagnostics, in purification of additional serine esterase, and in methods for inhibition of cytolysis and immunosuppression.

Inhibition of Cytolysis and Immunosuppression using Inhibitors of Murine Serine Esterase Inhibition of the esterase blocks cytolysis. Since the enzyme is normally intracellular, preliminary studies indicate that in vivo inhibition requires either that the inhibitor diffuse into the cell or that it be bound either to the target cell or to the CTL.

The serine esterase is specifically inhibited by serine esterase inhibitors, including DFP and PMSF. DFP was not tested for inhibition of cytolysis because propylene glycol, the solvent in which it is kept, is toxic for cells, but PMSF at nontoxic concentrations clearly inhibits lysis of P815 ($H-2^d$) cells by the cloned anti-$D^d$ G4 cells.

To measure cytolytic activity, the cells are incubated with inhibitors (or controls) for 30 minutes at 37° C., washed, counted, and diluted for titration of cytotoxic activity against $1 \times 10^4$ $^{51}$Cr-labeled P815 cells. Recovery of G4 is comparable for all the treated samples. In some experiments, DMSO alone is responsible for about 10-15% $^{51}$Cr release from labeled G4 cells but the presence of PMSF at the concentrations shown has no added toxicity as measured either by $^{51}$Cr release or by reduced recovery of viable (trypan blue-negative) G4 cells. CTL assays were performed as described by E. Celis, A. H. Hale, J. H. Russell, and H. N. Eisen in *J. Immunol.*, 122, 954-958 (1979).

The inhibition of cytolytic activity is shown in FIG. 1. The G4 cells were suspended in complete medium at about $5 \times 10^6$/ml and DMSO (control) or PMSF dissolved in DMSO was added to a final DMSO concentration of 3%. 0--0, control with DMSO alone; — . 0.375 mM PMSF; . — . 0.75 mM PMSF — , 1.5 mM PMSF; — . 3 mM PMSF. The results are expressed as a dose-response curve. One lytic unit ($LU_{50}$) is the number of CTL required for 50% specific lysis of $1 \times 10^4$ $^{51}$Cr-labeled P815 cells. Percent inhibition = $(1 - [LU_{50}$ in presence of PMSF/$LU_{50}$ in absence of PMSF]) $\times 100$.

These data demonstrate the inhibition of murine CTL activity by low molecular weight inhibitors of serine esterase. In contrast, protein inhibitors of serine esterases and soluble anti-serine esterase antibodies have not been potent inhibitors of CTL-mediated lysis. Aprotinin, a peptide inhibitor of 6513 daltons and a potent inhibitor in vitro of purified BLT serine esterase, does not inhibit CTL-mediated lysis even when present in the medium at 667 μg/ml, approximately $10^{-4}$ M aprotinin. However, when aprotinin is covalently attached to the membrane of target cells, it appears to inhibit cytotoxicity, as shown by FIG. 2, comparing lysis of modified P815 target cells (measured as % specific Cr release) as a function of the ratio of effector cell to target cell (0.25, 0.5, 1, 2, 4, 8, 16:1).

To assay inhibition of CTL-mediated lysis by soluble aprotinin, 67 μl aliquots dissolved in PBS (containing 62.5 μg/ml - 2 mg/ml aprotinin) were added to 67 μl of CTL G4 and incubated on ice for 15 minutes. Ten thousand $^{51}$Cr-labeled P815 cells (in 67 μl) were then added and lysis at E:T ratios of 0.5-4 was quantitated after 4 hour incubation at 37° C. The final aprotinin concentration was 20.8-667 μg/ml.

Aprotinin was covalently coupled to target cells according to the following protocol. First, aprotinin (2 mg/ml) was reacted with SPDP (N-succinimidyl 3-(2-pryidiyldithio)propionate) in PBS at room temperature for 7 minutes. ε-amino caproic acid was added to quench the reaction, and the reaction mixture was dialysed against 2 1-liter changes of PBS over 24-48 hours. After radiolabeling P815 target cells with Na$^{51}$Cr$_2$O$_3$, the cells were washed twice in PBS and incubated in Traut's reagent (2-iminothiolane, 10 mM final concentration) and dithiothreitol (0.5 mM) for 10 minutes. The cells were washed twice in PBS and resuspended in PDP-aprotinin for 1 hour at room temperature. After 2 additional washes, they were added to G4 CTL. Standard 4 hour cytotoxicity assays were performed. Control P815 target cells were prepared by incubating radiolabeled cells in PBS alone or in PDP-ribonuclease instead of PDP-aprotinin.

The serine esterase which is unique to CTL can be used as a basis for specific immunosuppression. In the preferred embodiment, specific inhibitors of the serine esterase are bound either to the CTL or to the target cell. The inhibitor can be bound using a molecule which specifically inhibits the enzyme in combination with a molecule which specifically binds to a molecule on the surface of either the target cell or the CTL, such as an antibody to the mouse Thy-1 antigen or the human CD2, CD5, or CD6 antigens. Preferred antibodies or antigen binding antibody fragments are those which do not activate complement or other components which result in lysis and are not recognized by antibody dependent killer cells. Preferred inhibitors are those which are not overly toxic to normal cells. Aprotinin is the preferred inhibitor at this time since it has been infused clinically in the treatment of pancreatitis and will not diffuse into normal cells, yet can be specifically bound to the surface of either the target cells or CTLs using a coupled binding molecule.

Anti-esterase antibodies should also be useful in inhibiting cytolytic activity by the CTL's in vivo. Specifically, monoclonal anti-esterase antibodies are injected into a patient to be immunosuppressed according to methods known to those skilled in the art. Such methods are taught by A. B. Cosimi et al. in "Treatment of Acute Renal Allograft Rejection with OKT3 Monoclonal Antibody" in Transplantation, 32, 535-539 (1981) and "The Use of Monoclonal Antibodies to T Cell Subsets for Immunological Monitoring and Treatment in Recipients of Renal Allografts" in *N. E. J. Med.*, 305, 308-315 (1981). In both of these examples, monoclonal antibodies to surface T-cell antigens were intravenously infused into human patients to reverse graft rejection.

These chemical immunomodulating agents selective for the serine esterase may provide a means for avoiding the side effects and complications which are presently unavoidable with the broad spectrum immunosuppressives such as the corticosteroids and cyclosporin.

Isolation and Characterization of Nucleotide Sequences encoding the Serine Esterase The esterase genes may also be cloned using methods familiar to those skilled in the art. Standard techniques such as those described by T. Maniatis, E. F. Fritsch, and J. Sambrook in *Molecular Cloning: A Laboratory Manual* (Cold Spring Harbor Laboratory, 1982) are used to purify polyadenylated RNA from G4 RNA using oligo dT chromatography, to generate cDNA by reverse transcriptase, to convert the cDNA to double stranded DNA using RNase H and DNA polymerase, to methylate the ds DNA product, and to attach linker oligonucleotide EcoRI sites for insertion into a lambda phage.

The genes encoding the esterase are cloned using a lambda phage such as the lambda gt 11 recombinant DNA expression vector described by Young and David in *Proc. Natl. Acad. Sci. USA*, 89, 1194-1198 (1983). The cDNA inserts are ligated into the EcoR1 site present in the beta gal Z gene. The resulting lambda gt 11 recombinant DNA library is used to infect a high frequency lysogenization strain. Host cells are blotted onto a nitrocellulose filter and replica plates made. Lysogens are induced, and the nitrocellulose filters probed with the Ig fraction of the rabbit antisera against both native protein and against individual polypeptide chains and with $^{125}$I protein A. Positive clones are purified, and their inserts isolated by Eco R1 digestion. The inserts are ligated into pBR322 plasmids. The plasmids are used to obtain sufficient quantities of the cloned inserts for restriction mapping and sequence determination by the Maxam-Gilbert method.

Alternatively, the sequences encoding the serine esterase can be determined by sequencing the purified protein and preparing oligonucleotide probes which are then used to screen a CTL cDNA library. Masson, et al., reported in FEBS 208(1), 84-86 (1986), after the filing date of applicants' application disclosing and claiming the serine esterase, U.S. Ser. No. 750,323 filed June 28, 1985 entitled "Cytotoxic T Lymphocyte Serine Esterase and Method for Stimulation and Inhibition", now U.S. Pat. No. 4,783,410, which the present application is a continuation-in-part of, the sequencing of the murine serine esterase of the present invention and its similarity to the CTL-specific gene (H-factor gene) reported by Gershenfeld and Weissmann, in *Science* 232,854-858 (1986), also after the filing date of U.S. Ser. No. 750,323.

Isolation and Characterization of Human Serine Esterase

Human CTLs have a serine esterase homologous to the murine enzyme, albeit at about one-tenth the level found in the corresponding murine cloned cell lines. Hemolytic activity, present in the murine cell lines, was not found in the human cells. It is notable that although perforin is not obviously conserved in human CTL, the BLT serine esterase appears to be conserved across these species.

The following materials and methods were used to isolate and characterize the human CTL serine esterase.

Mixed Lymphocyte Culture

Venous blood was sterilely collected from human volunteers and anticoagulated with sodium heparin (25 U/ml; Ellins-Sims, Inc., Cherry Hill, NJ); the blood was mixed with an equal volume of RPMI 1640, then layered over Ficoll-Hypaque (Pharmacia Fine Chemicals, Piscataway, NJ) and centrifuged at 2,500 rpm for 15 min. Cells at the Ficoll-serum interface were collected, washed twice with RPMI, and resuspended at a concentration of $10^6$ cells/ml in the presence of $5 \times 10^5$/ml irradiated (45 Gy) allogeneic EBV-transformed B cells, in KH medium (RPMI 1640, 6mM Hepes, 0.06 mM 2-ME [Sigma Chemical Co., St. Louis, MO], 1.6 mM L-glutamine, 100 U/ml penicillin, and 100 μg/ml streptomycin (Gibco Laboratories, Grand Island, NY). 10% heat-inactivated pooled human serum (Flow Laboratories, Inc., McLean, VA). After 5–7 days, lymphocytes were cloned by limiting dilution.

Rheumatoid Synovial Membrane

Synovial membranes were obtained from patients undergoing joint replacement for rheumatoid arthritis in accordance with the human studies guidelines of the Massachusetts Institute of Technology and the Massachusetts General Hospital. Membranes were placed in K medium (the same as KH medium, except that 10% heat-inactivated FCS is substituted for human serum) with 30 U/ml rIL-2, and after 1 wk cells in the supernatant were cloned by limiting dilution.

CTL Cloning by Limiting Dilution

Aliquots from the bulk T cell cultures were diluted to 10 viable cells/ml in KH medium to which was added 5% PHA supernatant, 50 U/ml human rIL-2 (the gift of Biogen Research Corp., Cambridge, MA), and B cells plus cells from the bulk MLC (each at $5 \times 10^5$ cells/ml and irradiated with 45 Gy). The mixture was distributed into flat-bottomed 96-well culture plates (Costar, Cambridge, MA) at 0.1 ml/well, equivalent to 1 viable cell/well. After 7 and 14 days an additional 0.1 ml of KH medium supplemented with PHA supernatant (5%), IL-2 (50 U/ml), and irradiated (45 Gy) B cells ($7.5 \times 10^5$/ml) was added to each well. Clones were generally visible after 10–20 days and were then expanded into 24-well culture plates. Clones were gradually weaned to KH medium supplemented with 5% PHA supernatant and 20–25 U/ml rIL-2, and restimulated at five-10 day intervals. The added B cells were allogeneic EBV-transformed cells.

Other Cell Lines

JY (HLA-A2,-B7) was obtained from the Tissue Culture Center at MIT, and CCRF-SB (HLA-A1,2-B12,17-Cw2) and RPMI 7666 (HLA-A3,w29,-B7,12) were obtained from the American Type Culture Collection (Rockville, MD). JY and CCRF-SB were derived by EBV transformation of peripheral blood lymphocytes; RPMI 7666 is a B cell lymphoma line. 6B-7 is a CTL clone derived from a transplanted kidney during an episode of rejection and was the gift of Dr. James Kurnick, Massachusetts General Hospital.

Cytotoxicity Assays $^{51}$Cr-release killing assays were performed as described; when measuring lectin-dependent cytolytic activity, Con A (Vector Laboratories, Inc., Burlingame, CA) was added to a final concentration of 10 μg/ml.

PMSF Inhibition of Cytolysis

Various numbers of T cells were incubated for 15 min at 37° C. in K medium containing PMSF at 0, 2, 4, and 6 mM (PMSF was added in DMSO; the final concentration of DMSO in all instances was 1%). Cytotoxicity was assayed as above except that a 2 hour assay was used to minimize the effect of new protein synthesis.

T Cell Surface Markers mAbs to CD3, CD4, and CD8 (OK-T3, OK-T4 and OK-T8, Ortho Diagnosic Systems, Inc., Westwood, MA) and FITC-labeled rabbit anti-mouse (Fab')$_2$ (Cooper Biomedical, Inc., Malvern, PA) were used to stain T cells, which were then analyzed by fluorescence microscopy or in an Ortho Diagnostic Systems, Inc. 50 H flow cytometer.

Serine Esterase Activity

Enzyme levels were determined as previously described.

Table 2 summarizes the levels of BLT-serine esterase found in NP-40 lysates of 20 human T cell lines. All but three (1E-12, ML-47.2, and 5D-4) were cytotoxic, exhibiting 30–80% specific lysis of Cr-labeled target cells during a 4-h assay at a CTL/target ratio of 20:1. For comparison, three human B cell lines and one murine CTL were also assayed. The murine CTL 2C, had an enzyme level (94 U/$10^6$ cell equivalents) similar to that previously described for other cloned murine CTLs. The human B cell lines had only trace activity in the BLT assay (<0.5 U/$10^6$ cells). In contrast, the level of serine esterase in human cytolytic T cells ranged from 3.9–21 U/$10^6$ cells, with an average of 9.1 U/$10^6$ cells; no consistent difference was seen between CD4$^-$ and CD8$^-$ cell lines. While the levels in three noncytotoxic CD4$^-$ human T cell lines were perhaps slightly lower than in cytotoxic T cells, they were distinctly higher than in non-T cells; this is in contrast to murine T cell lines in long-term culture, where the enzyme levels in nearly all noncytotoxic (CD4$^-$) T cells is <1% of the level in cytotoxic T cells. However, the level of esterase activity seen in all the human CTL clones was consistently lower than in murine CTLs.

The levels of BLT-serine esterase activity are very low in murine thymocytes, but increase more than 50-fold after activation by Con A, in parallel with the appearance of cytotoxic activity. Similarly, the enzyme levels in fresh human peripheral blood lymphocytes were also very low (approximately 0.5 U/$10^6$ cells), but increased along with the appearance of specific cytolytic activity during the course of a mixed lymphocyte culture, to 1.5 U/$10^6$ cells after 5 d and 3.8 U/$10^6$ cells after 12 d.

TABLE 2

| Cell Line | BLT-DTNB Assay for Serine Esterase Activity in Human Lymphocytes | | | |
|---|---|---|---|---|
| | Source | Type | Specificity[a] | Esterase Level U/$10^6$ Cells |
| JY | EBV-pbl[b] | B cell | — | 0.2 |

TABLE 2-continued

BLT-DTNB Assay for Serine Esterase Activity in Human Lymphocytes

| Cell Line | Source | Type | Specificity[a] | Esterase Level U/10⁶ Cells |
|---|---|---|---|---|
| CCRF-SB | EBV-pbl | B cell | — | 0.3 |
| RPMI 7666 | Lymphoma | B cell | — | 0.1 |
| 2C | Murine CTL[c] | CD8+ | H2-L[d] | 94 |
| HE-14 | MLCd | CD4+ | JY | 11.7 |
| HE-17 | MLC | CD4+ | LDK | 4.2 |
| HEJ-20 | MLC | CD4+ | JY | 21.0 |
| ML-21 | MLC | CD4+ | JY,CCRF-SB | 19.4 |
| HEB-13 | MLC | CD8+ | HLA-B7 | 9.9 |
| HEB-34 | MLC | CD8+ | HLA-A2 | 5.8 |
| ML-4 | MLC | CD8+ | HLA-A2 | 4.1 |
| ML-32 | MLC | CD8+ | HLA-B7 | 4.6 |
| ML-37.4 | MLC | CD8+ | HLA-A2 | 15.4 |
| 1B-1 | MLC | CD8+ | LDK | 9.6 |
| 1B-6 | MLC | CD8+ | LDK | 4.4 |
| 1D-12 | MLC | CD8+ | CCRF-SB | 3.1 |
| 5C-5 | MLC | CD8+ | LDK | 7.5 |
| 1B-5 | MLC | CD8+ | LDK | 4.2 |
| 1A-3 | MLC | CD8+ | LDK | 3.9 |
| 1D-1 | Synovium | CD8+ | LDK | 13.0 |
| 6B-7 | Renal graft | CD8+ | | 11.4 |
| 1E-12 | Synovium | CD4+ | Non-killer | 3.4 |
| ML-47.2 | MLC | CD4+ | Non-killer | 5.6 |
| 5D-4 | MLC | CD4+ | Non-killer | 2.2 |

[a]Where appropriate, specificity was determined in a 4-h ⁵¹Cr— release assay using various B-cell lines as targets. LDK, lectin-dependent killer, denotes cells cytolytic only in the presence of Con A.
[b]Epstein-Barr virus transformed peripheral blood lymphocyte.
[c]A murine CTL clone is included for comparison with the human cell lines.
[d]Mixed lymphocyte cultures were used to elicit the CTL lines listed in column 1.

CTL Membranes

10⁹ cells of a cloned human CTL cell line, HE-14, were harvested and the membranes purified and solubilized with 0.5% NP-40 in PBS as previously described: about 97% of the total BLT-esterase activity present in the cell lysate resided in the pelleted membranes.

Inhibition of Serine Esterase Activity

Aliquots of NP-40 solubilized HE-14 membranes containing about 1 U of BLT-esterase activity were diluted to 0.1 ml with 0.5% NP-40 in PBS, and 2 µg of the following inhibitor solutions were added: PMSF, 100 mM in DMSO; N-α-p-tosyl L-lysine chloromethyl ketone (TLCK), 25 mM in DMSO; N-tosyl-L-phenylalanine chloromethyl ketone (TPCK), 25 mM in DMSO; and diisopropylfluorophosphoridate (DFP), 100 mM in propylene glycol. After 30 min at 37° C., serine esterase activity was measured as above.

One of the distinguishing features of the murine T cell-specific serine esterase is its pattern of susceptibility to protease inhibitors: it is inhibited by PMSF and DFP, but not by TLCK or TPCK. Similarly, after a 20-min incubation at room temperature with 2mM PMSF, the human BLT-serine esterase was almost completely inhibited (97% reduction in esterase activity), whereas a similar incubation with 0.5 mM TLCK or 0.5 mM TPCK did not significantly inhibit the enzyme (−1% and 4% inhibition, respectively) (Table 3). A single addition of 2 mM DFP resulted in only 34% inhibition, probably because of instability of DFP in an aqueous environment at pH 8; increased inhibition (to 68%) was seen with a second addition of DFP. As with murine CTLs, preincubating intact human cTLs with PMSF markedly decreased the H cytolytic activity in a 2-h ⁵¹Cr-release assay; 15 min in 6 mM PMSF reduced cytotoxicity by approximately 75%, while not affecting the viability of either the CTLs (as assessed by trypan blue exclusion) or the targets (as assessed by release of ⁵¹Cr).

TABLE 3

Inhibition of Human CTL Clone HE-14 Serine Esterase Activity

| Inhibitor | Concentration mM | Esterase Activity OD₄₁₂ | Inhibition % |
|---|---|---|---|
| None | — | 0.608 | — |
| PMSF | 2.0 | 0.018 | 97 |
| TLCK | 0.5 | 0.615 | 1 |
| TLCK | 0.5 | 0.585 | 4 |
| DFP | 1 × 2.0 | 0.403 | 34 |
| DFP | 2 × 2.0 | 0.192 | 68 |

SDS-PAGE of DFP-labeled Cell Extracts 0.4 ml of NP-40 extracts of the murine CTL cell line G4 or of HE-14 cell membranes were labeled with 20 µCi of 1,3-[³H]DFP in propylene glycol (5.2 Ci/mmol; New England Nuclear, Boston, MA) as described, and subjected to discontinuous SDS-PAGE on a 10% gel as per Laemmli. Gels were briefly stained with 0.1% Coomassie Brilliant Blue (Bio-Rad Laboratories, Richmond, CA) to locate molecular weight markers, then after destaining were impregnated with Autofluor (National Diagnostics, Inc., Somerville, NJ), dried, and exposed at −70° C. on Kodak XAR-5 film (Eastman Kodak Co., Rochester, NY).

pH Optimum of Serine Esterase Activity Aliquots containing approximately one unit of BLT-serine esterase were diluted to 0.1 ml with buffered saline (130 mM of NaCl, 20 mM Tris phosphate, pH ranging from 5.0–9.5), 10 µl of 20 mM BLT was added, followed after 30 min at room temperature by 0.9 ml of 2.2 mM 5,5'-dithiobis-(2-nitrobenzoic acid) (DTNB) in 300 mM Tris Cl, pH 8.1. The absorbance at 412 nm was determined 30 seconds later, to allow ample time for the cleaved BLT to react with the DTNB without having significant amounts of additional enzymatic cleavage of the BLT. At each pH value, the spectrophotometer was blanked to an identically treated sample free of added esterase, to control for any pH effect on the spontaneous hydrolysis of BLT.

The pH optimum for the BLT-serine esterase activity in murine CTLs is about 8, much higher than the optimal pH for macrophage esterases (pH 3–4). The activity of the serine esterases from HE-14 cell membranes and 2C whole-cell lysates was measured at various pH values ranging from 5 to 9.5. For both enzymes, activity was negligible at pH 5, and increased in parallel to a maximum at pH 8–9.

Dot Blot Analysis of cDNA Inserts

To further characterize the human BLT-serine esterase, a lambda gt 10 phage cDNA library was constructed from the human cloned CTL line HE-14 as described, and screened with a mixture of [³²P]kinase-labeled oligonucleotide probes corresponding to the regions around the active site serine and histidine residues of the murine HF and C11 genes. The cDNA insert from one of the identified clones was compared by dot blot analysis with the insert of a murine cDNA clone known to have a C11 sequence using the individual oligonucleotide probes.

The cDNA library constructed from the human CTL line HE-14 was screened with a mixture of synthetic oligodeoxynucleotide probes corresponding in sequence to the regions around the active site serine (Ser) and histidine (His) residues of the murine serine esterase genes termed HF and C11. Dot blots of the insert from one of the strongly hybridizing cDNA clones, together with a previously isolated murine cDNA clone having a sequence identical to the published sequence for murine C11, were separately hybridized with each of the oligonucleotide probes. The human cDNA clone hybridized strongly with the His probe from the murine HF gene but not with the His probe from the murine C11 gene, indicating homology between the human cDNA clone and the murine HF gene. The intensity of hybridization to the Ser probes also support this conclusion, although less definitively because the probes cross-hybridize with both the murine HF and C11 genes.

Serine Esterase Secretion by Human CTLs

CTLs and $^{51}$Cr-labeled JY targets were suspended in RPMI 1640 plus 1 mg/ml BSA (Boehringer Mannheim Diagnostics, Inc., Houston, TX): $8 \times 10^5$ CTLs in 0.1 ml were added to a variable number of target cells (also in 0.1 ml) to give final CTL/target ratios ranging from 4:1–0.25:1. After 3 hours at 37° C., the supernatants from duplicate wells were pooled: 50 $\mu$l were taken to determine serine esterase activity, and 75 $\mu$l taken to measure release of $^{51}$Cr. Total esterase activity in the CTLs was determined from NP-40 lysates: the baseline esterase activity from JY alone (which is mostly composed of reducing activity rather than enzymatic activity) was determined by incubating targets without CTLs and treating as above.

Many murine CTLs release some (10–60%) of their total serine esterase activity into the medium when they interact with an excess of their target cells. Two human CTL lines (HE-14, HEJ-20) were similarly tested for serine esterase secretion when incubated with up to a fourfold excess of the appropriate $^{51}$Cr-labeled labeled target cells. No significant release of BLT-serine esterase activity into the medium was detected over 3 h, although considerable target cell lysis (as high as 0.8 target cell lysed per CTL) was observed.

Percoll Density Gradient Centrifugation

CTLs were harvested, washed with PBS, resuspended in relaxation buffer (0.1 M KCl, 3 mM NaCl, 3.5 mM MgCl$_2$, 1.25 mM EGTA (Signal Chemical Co.), 10 mM Pipes.pH 6.8, with ATP (both Sigma Chemical Co.) added to 1 mM just before use and subjected to Percoll density gradient centrifugation as described. After centrifugation, 0.8 ml fractions were collected from the bottom of the tube using capillary tubing attached to a peristaltic pump. To detect serine esterase activity, 20–25 $\mu$l aliquots of each fraction were placed in 96-well flat-bottomed assay plates (Immulon-1: Dynatech Laboratories, Inc., Alexandria, VA) and 0.125 ml of a standard reaction mixture (0.1 mM BLT, 1 mM DTNB in 300 mM TrisCl, pH 8.1) was added to each well. After 5 min at room temperature, the absorbance at 414 nm was measured using a Titertek Multiskan scanner (Flow Laboratories, Inc.) blanked to relaxation buffer plus reaction mixture alone. Hemolytic activity in 10–50 $\mu$l aliquots was measured as described using as targets either sheep erythrocytes (Colorado Serum Co., Boulder, CO: stored at 4° C. in Alsevier's solution, then washed and resuspended in Hepes-buffered saline just before use) or fresh human erythrocytes (collected sterilly into sodium-heparin, 25 U/ml, then washed and resuspended in Hepes-buffered saline). Approximately $3 \times 10^7$ erythrocytes were used for each sample. The absorbance of released hemoglobin was measured at 414 nm on a Titertek Multiskan scanner blanked to PBS.

When disrupted by nitrogen cavitation and subjected to discontinuous Percoll gradient centrifugation, murine CTLs exhibit both a large high-density peak of BLT-serine esterase activity that coincides with the peak of hemolytic activity, and a small low-density peak of BLT-serine esterase activity. Seven human CTL lines (two CD4+, five CD8+) were similarly analyzed by Percoll density centrifugation. Each gradient exhibited two peaks of activity, with the high-density peak being only about the same size as the low-density peak, instead of much larger as with murine CTLs.

Freeze-Thaw Assay for Hemolytic Activity $5 \cdot 10^6$ CTLs (HE-14, ML-4) or murine CTLs (2C) were washed twice in PBS plus 1 mM EDTA, then resuspended in 0.05 ml of the same buffer. Samples were frozen in a dry ice-ethanol bath for 10 min, then thawed in cold water, centrifuged for 5 min at 8,000 rpm and 4° C., and the supernatants were stored on ice until assayed. Aliquots of supernatants obtained after one, two, and three freeze-thaw cycles were tested for hemolytic activity as above.

None of the Percoll gradients contained any hint of hemolytic activity, even when the aliquots tested were 20 times larger than those sufficient to demonstrate considerable hemolysis from murine CTL lines. To test the possibility that this lack of hemolytic activity was due to the presence of an inhibitor, rather than the absence of the hemolytic protein per se, $10^8$ HE-14 cells were mixed with $2 \cdot 10^7$ murine CTL (2C) cells, and the mixture subjected to nitrogen cavitation and Percoll density centrifugation. The amount and position of the peak with hemolytic activity from the murine CTL 2C matched the results from gradients prepared from 2C alone, and coincided with the high-density serine esterase peak.

Therefore, the absence of hemolytic activity in the human CTL lysate was not due to the presence of an inhibiting substance, at least not one that was also capable of inhibiting the murine hemolytic activity. The location of the murine and human high-density BTL-serine esterase peaks coincided in this study and also when separate gradients of murine cells and HE-14 were run in parallel.

To look for hemolytic activity by an alternative method, suspensions of freeze-thawed cells from two human CTL lines (HE-14, ML-4) were assayed in parallel with the murine CTL line 2C. As can be seen in Table 4, the hemolytic activity from murine CTLs is easily detected in this manner; in contrast, detectable hemolytic activity was not released from the human CTLs.

TABLE 4

Hemolytic Activity After Freeze-Thaw Lysis of Murine and Human CTLs

| Number of Freeze-Thaw Cycles | CTL Cell Equivalents Tested | 2C (Murine) OD$_{414}$ | % | HE-14 (Human) OD$_{414}$ | % | ML-4 (Human) OD$_{414}$ | % |
|---|---|---|---|---|---|---|---|
| 1 | $2 \cdot 10^5$ | 2.073 | 85 | 0.056 | −1 | 0.062 | −1 |
|   | $1 \cdot 10^6$ | 2.379 | 98 | 0.059 | −1 | 0.058 | −1 |
|   | $2.5 \cdot 10^6$ | 2.369 | 98 | 0.053 | −1 | 0.057 | −1 |
| 2 | $2 \cdot 10^5$ | 0.415 | 15 | 0.068 | 0 | 0.051 | −1 |
|   | $1 \cdot 10^6$ | 2.312 | 96 | 0.046 | −1 | 0.057 | −1 |

TABLE 4-continued

Hemolytic Activity After Freeze-Thaw Lysis of Murine and Human CTLs

| Number of Freeze-Thaw Cycles | CTL Cell Equivalents Tested | Hemoglobin Release (Specific Hemolysis) | | | | | |
|---|---|---|---|---|---|---|---|
| | | 2C (Murine) | | HE-14 (Human) | | ML-4 (Human) | |
| | | $OD_{414}$ | % | $OD_{414}$ | % | $OD_{414}$ | % |
| 3 | $2.5 \times 10^6$ | 2.397 | 99 | 0.050 | −1 | 0.051 | −1 |
| | $2 \times 10^5$ | 0.148 | 3 | 0.055 | −1 | 0.069 | 0 |
| | $1 \times 10^6$ | 1.710 | 70 | 0.050 | −1 | 0.058 | −1 |
| | $2.5 \times 10^6$ | 2.152 | 89 | 0.054 | −1 | 0.059 | −1 |

Detergent lysis of erythrocytes, which resulted in an absorbance of 2.416, was taken as 100% hemolysis; untreated erythrocytes (spontaneous hemolysis) resulted in an absorbance of 0.074.

SDS-PAGE of [³H]DFP Labeled BLT-Serine Esterase

Because human CTLs exhibit less BLT-serine esterase activity than murine CTLs, only limited amounts of [³H]DFP affinity-labeled enzyme from unfractionated cell lysates could be loaded onto a gel. To overcome this limitation, NP-40 solubilized HE-14 cell membranes (which contained approximately 97% of the BLT-serine esterase activity present in these cells) were labeled and subjected to SDS-PAGE under reducing and nonreducing conditions; similarly labeled extracts of the murine CTL line G4 were included for comparison. Under reducing conditions the tritium label from HE-14 appeared predominately in a band of $M_r$ $31 \times 10^3$; the murine cell extract shows a more diffuse band at $M_r$ $30-34 \times 10^3$. Under nonreducing conditions, the ³H-labeled proteins had a higher apparent molecular mass ($M_r$ approximately $51 \times 10^3$ for human and approximately $59 \times 10^3$ for mouse), indicating that the human enzyme, like the mouse enzyme, is probably a disulfide-linked dimer.

Taken together, all of these results show that cloned human T cell lines contain a homologue of the murine T cell-specific BLT-serine esterase. The human and murine enzymes are similar in several respects:
- both are expressed in T cells but not in B cells;
- they have similar patterns of inhibition by small organic molecules (i.e., they are inhibited by PMSF and DFP, but not by TLCK or TPCK);
- both enzymes can be affinity labeled with [³H]DFP, and have similar apparent molecular weights ($M_r$ approximately 30,000 for the human enzyme and 30-34,000 for the murine enzyme) by SDS-PAGE analysis under reducing conditions;
- a cDNA clone from a library prepared from a human cloned T cell line (HE 14) hybridizes with two synthetic oligonucleotide probes that correspond to nucleotide sequences surrounding the active site serine and histidine of the HF gene, which encodes the principal murine T cell-specific BLT-serine esterase; and
- the activity in human peripheral blood lymphocytes also increases after allogeneic stimulation, just as the BLT-serine esterase activity in murine thymocytes increases markedly after stimulation with Con A.

There are also some differences between the murine and human BLT-serine esterases. The enzyme level in the cloned human T cell lines is only about one-tenth that present in cloned murine CTLs; and, while the enzyme is expressed at high levels (30-200 U/$10^6$ cells) in cytolytic murine T cell lines but not in noncytolytic (helper) cloned murine T cell lines (which typically had $\leq$U/$10^6$ cells), the enzyme is present at about the same level in both human cytolytic (either CD4⁻, CD8⁻ or CD4⁻, CD8⁻) and human noncytolytic (CD4⁻, CD8⁻) lines. In view of a recent study showing that the CD8⁺ (Lyt-2⁺) and CD4⁺ (L3T4⁺) bulk T cell populations derived from 6 day mixed lymphocyte cultures in mouse cell lines have similar levels of BLT-serine esterase, despite substantial differences in cytolytic activity, it is possible that the differences between cytolytic and noncytolytic murine CTLs is a consequence of these cells having been maintained in culture for long periods (i.e., 1 to 5 yr). In contrast, the cloned human T cell lines tested here were in culture for no longer than 6 months. Most murine CTLs are triggered to secrete their BLT-serine esterase by interaction with target cells; two similarly stimulated human CTL clones did not release a detectable level of BLT-serine esterase during interaction with their target cells. The apparent molecular weights of the reduced and nonreduced [³H]DFP-labeled human enzyme are approximately 31,000 and 51,000, respectively, indicating that the esterase is found as a heterodimer consisting of a DFP-reactive subunit of approximately 31,000 $M_r$ and a non-reactive subunit of 20,000 $M_r$, in contrast to the murine enzyme, which is probably a homodimer. The possibility that the human enzyme is a homodimer with an unusually high electrophoretic mobility cannot be ruled out on the basis of this information.

Although the present invention, nucleotide sequences encoding a serine esterase predominantly found in cytolytic T lymphocytes, antibodies to the serine esterase, and methods for inhibiting cytolysis through inhibition of the serine esterase, has been described with reference to specific embodiments, it is understood that modifications and variations may occur to those skilled in the art. It is intended that all such modifications and variations be included within the scope of the appended claims.

What is claimed is:

1. An antibody specifically binding to an intracellular serine esterase wherein the serine esterase is produced by cytotoxic T lymphocytes and has an apparent molecular weight of approximately 28,000-31000 as determined by SDS gel electrophoresis under reducing conditions and trypsin-like activity inhibited by diisopropylfluorophosphate and phenylmethylsulfonyl fluoride but not inhibited by N-α- tosyl lysyl chloromethyl ketone at a concentration inhibiting the cytotoxicity of cytotoxic T lymphocytes.

2. The antibody of claim 1 wherein said antibody is directed against the serine esterase produced by human T lymphocytes.

3. The antibody of claim 1 wherein said antibody is directed against the serine esterase produced by mouse T lymphocytes.

4. A method for inhibiting lysis by cytolytic T lymphocytes comprising selectively inhibiting a serine esterase produced by cytotoxic T lymphocytes wherein said esterase has an apparent molecular weight of approximately 28,000-31,000, as determined by SDS gel electrophoresis under reducing conditions, and trypsin-like activity not inhibited by N-α-tosyl lysyl chloromethyl ketone at a concentration inhibiting the cytotoxicity of cytotoxic T lymphocytes, or a proteolytically active portion thereof, by specifically binding in vitro an inhibitor of the serine esterase to the serine esterase or its substrate.

5. The method for inhibiting lysis by cytolytic T lymphocytes of claim 4 wherein the serine esterase is selectively inhibited by monoclonal anti-esterase antibodies.

6. The method of inhibiting lysis by cytolytic T lymphocytes of claim 4 wherein the serine esterase is inhibited by specifically binding a low molecular weight non-protein serine esterase inhibitor to the serine esterase.

7. The method of inhibiting lysis by cytolytic T lymphocytes of claim 6 further comprising binding the serine esterase inhibitor to the cytolytic T lymphocyte.

8. The method of inhibiting lysis by cytolytic T lymphocytes of claim 7 wherein the inhibitor is coupled to a molecule which specifically binds to the surface of cytolytic T lymphocytes.

9. The method of inhibiting lysis by cytolytic T lymphocytes of claim 8 wherein the esterase inhibitor is coupled to an antibody or antibody fragment directed against an antigen specific to the surface of T lymphocytes, wherein binding of said antibody to a cell surface does not activate complement or antibody dependent killer cells.

10. The method of inhibiting lysis by cytolytic T lymphocytes of claim 6 further comprising binding the serine esterase inhibitor to the cells lysed by T lymphocytes sin the presence of the serine esterase.

11. The method of inhibiting lysis by cytolytic T lymphocytes of claim 4 wherein the inhibitor is coupled to a molecule which specifically binds to the surface of the cytotoxic T lymphocytes containing the serine esterase.

12. The method of inhibiting lysis by cytolytic T lymphocytes of claim 11 wherein said esterase inhibitor is coupled to an antibody or antibody fragment directed against an antigen specific to the surface of the cells lysed by T lymphocytes in the presence of the serine esterase, wherein binding of said antibody to a cell surface does not activate complement or antibody dependent killer cells.

* * * * *

UNITED STATES PATENT AND TRADEMARK OFFICE
CERTIFICATE OF CORRECTION

PATENT NO.   : 5,017,489
DATED        : May 21, 1991
INVENTOR(S)  : Mark S. Pasternack, Herman S. Eisen It is certified that error appears in the above-identified patent and that said Letters Patent is hereby corrected as shown below:

Title page, item [54]: Repalce "LYMPHOCTE" with --LYMPHOCYTE--.
Title page, after item [22], the filling date, insert the following:
   --[63]  Related U.S. Application Data
         Continuation-in-part of Ser. No. 750,323, June 28, 1985,
         Pat. No. 4,783,410.--
Col. 1, Title, line 1:  Replace "LYMPHOCTE" with --LYMPHOCYTE--.
Col. 5, line 65:  Replace "(RCASUp)" with --(RCASUP)"--.
Col. 8, lines 62, 63:  Replace lines 62 and 63 with "●—●, 0.375 mM PMSF; ▲—▲, 0.75 mM PMSF; ■—■, 1.5 mM PMSF;-▼—▼-, 3 mM--.
Col. 13, line 65:  Delete "H".
Col. 14, line 29:  Place a period --.-- after "Activity", and make "pH Optimum of Serine Esterase Activity." a header. Move "Aliquots" to beginning of line 30.
Col. 18, line 1:  Replace "$\leq U/10^6$" with --$\leq 1U/10^6$--.
Col. 20, line 6:  Replace "sin" with --in--.

Signed and Sealed this

First Day of November, 1994

Attest:

BRUCE LEHMAN

*Attesting Officer*       *Commissioner of Patents and Trademarks*